United States Patent [19]

Mecca

[11] 4,181,804
[45] Jan. 1, 1980

[54] ALLANTOIN UROCANIC ACID COMPLEXES

[75] Inventor: Sebastian B. Mecca, Abington, Pa.

[73] Assignee: Carroll Products, Inc., Philadelphia, Pa.

[21] Appl. No.: 2,289

[22] Filed: Jan. 10, 1979

[51] Int. Cl.$^2$ .................. A61K 7/42; C07D 233/88
[52] U.S. Cl. ................... 548/311; 424/59; 424/273 R
[58] Field of Search .................................. 548/311

[56] References Cited

U.S. PATENT DOCUMENTS

| | | | |
|---|---|---|---|
| 3,107,252 | 10/1963 | Lubowe | 548/311 |
| 3,275,643 | 9/1966 | Lubowe | 548/311 |
| 3,290,323 | 12/1966 | Lubowe | 548/311 |
| 3,290,324 | 12/1966 | Lubowe | 548/303 |
| 3,305,557 | 2/1967 | Lubowe | 548/311 |
| 3,578,656 | 5/1971 | Mecca | 536/121 |
| 3,632,596 | 1/1972 | Mecca | 260/299 |
| 3,898,243 | 8/1975 | Mecca | 548/311 |
| 3,927,021 | 12/1975 | Mecca | 548/311 |
| 3,954,989 | 5/1976 | Mecca | 424/273 R |
| 3,970,748 | 7/1976 | Mecca | 424/68 |
| 3,970,756 | 7/1976 | Mecca | 424/273 R |
| 4,025,525 | 5/1977 | Takayama et al. | 548/311 |

OTHER PUBLICATIONS

Urocanic Acid published by Ajinomoto Co., Inc., Tokyo, Japan.

*Primary Examiner*—Natalie Trousof
*Attorney, Agent, or Firm*—Steele, Gould & Fried

[57] ABSTRACT

Allantoin urocanic acid complexes and cosmetic compositions containing these complexes are disclosed.

2 Claims, No Drawings

4,181,804

ALLANTOIN UROCANIC ACID COMPLEXES

BACKGROUND OF THE INVENTION

Allantoin is recognized as possessing soothing, keratolytic, moisturizing and anti-irritant properties. Allantoin salts and allantoin complexes are the subject of U.S. Pat. Nos. 3,107,252; 3,275,643; 3,290,323; 3,290,324; 3,305,557; 3,578,656; 3,632,596; 3,898,243; 3,927,021; 3,954,989; 3,970,748; and 3,970,756.

Urocanic acid is a metabolite derived from histidine. It is found in human sweat and mammalian epidermis, and is reported to have a role in protecting skin from ultraviolet light. A description of urocanic acid, its properties and uses is found in an article entitled Urocanic Acid published by Ajinomoto Co., Inc. of Tokyo, Japan. This article points out that urocanic acid may be effective as a natural sun screen in cosmetics. It is known, however, that alkaline salts, especially sodium salts of urocanic acid exhibit a high solubility in water but that such solutions undergo relatively rapid changes in color when exposed to sunlight or heat. Urocanic acid in epidermis is said to absorb 50% of ultraviolet radiation to which it is exposed.

It is an object of this invention to provide novel complexes of allantoin and urocanic acid which are not sensitive to sunlight or heat and which may be used in a variety of cosmetic formulations for beneficial effects.

DETAILED DESCRIPTION OF THE INVENTION

The present invention relates to novel complexes of allantoin and urocanic acid, and, more particularly to an allantoin urocanic acid complex, an allantoin urocanic acid salt complex and to cosmetic compositions containing these complexes. The complexes of the invention may be depicted as having the formulas:

$[C_4H_5N_4O_3]_a \cdot [C_6H_6N_2O_2]_b$ (allantoin urocanic acid complex);

$[C_4H_5N_4O_3]_a \cdot [C_6H_6N_2OX]_b$ (allantoin urocanate complex);

wherein a and b are each about 1 and refer to the number of mols of each component and X is a member selected from the group consisting of sodium, potassium and ammonium.

The complexes are prepared by thoroughly mixing allantoin with urocanic acid forming a semidry mass which is oven dried to provide the desired complex. Alternatively, allantoin and urocanic acid may be dissolved in an alkali metal hydroxide solution, acidified to precipitate the desired complex and oven dried. Allantoin and urocanic acid are available commercially, and are used in such form in preparing the complexes of this invention.

As mentioned, allantoin is known to possess soothing, cleansing, healing, moisturizing, anti-irritant and skin softening properties, and urocanic acid is recognized as a natural ultraviolet absorber contained in human sweat. Urocanic acid (imidazole-4-acrylic acid), exists in trans and cis isomeric forms. Natural urocanic acid consists of the trans isomer with slight contamination of the cis isomer. The trans isomer is slightly soluble in water, slightly more soluble in boiling water, but almost insoluble in organic solvents. The maximum absorption of ultraviolet light by urocanic acid varies with the pH of solutions of the acid, with maximum absorption of 28–290 mu occuring with solutions having a pH of 7 to 7.5.

Allantoin and urocanic acid or alkali metal salts or urocanic acid are preferably combined in a mol ratio of about 1:1. In preferred embodiments of the invention, allantoin and urocanic acid are combined in a mol ratio of about 1:1 to form allantoin urocanic acid complex. Likewise, allantoin and sodium, potassium or ammonium urocanate are combined in a mol ratio of about 1:1 to form an allantoin urocanic complex.

Elevated temperatures are required for formation of the desired complexes. Thus, the reaction mixtures are heated to temperatures of from about 160° to 180° F. for about 10 to 12 hours during formation of the complexes.

The complexes of this invention have the combined attributes of the healing anti-irritant cleansing, emollient, moisturizing and skin softening properties of allantoin, and the ultraviolet absorption (sun screening) properties of urocanic acid. Remarkably, the complexes of this invention have been found to pose no problem of skin irritation. Quantities effective to absorb about 100% of the ultraviolet rays of the sun, and thus are significantly more effective than conventional ultraviolet absorbers. Also, the complexes surprisingly have been found to be soluble in organic solvent including alcohol, thus permitting the formation of topical compositions with a urocanic acid content capable of maximum absorption of ultraviolet light.

The complexes are useful in solution form or in lotions or creams, where they demonstrate the ability to maintain tissue moisture balance when the skin is exposed to ultraviolet rays of the sun. The complexes prevent severe burning of the skin through absorption of ultraviolet rays while allowing controlled tanning of the skin. At the same time, the complexes permit the skin to remain moisturized, supple and soft and reduce possible blemishes resulting from exposure to the sun's rays. Generally, the complexes are formulated in pharmaceutically acceptable carriers at levels from 4 to 10 percent, by weight, based on the weight of the product, to form the desired sun screening lotions and creams.

The following examples illustrate properties of the complexes of this invention and suggested uses for the complexes. The examples are illustrative only, and not intended to limit the scope of the invention.

EXAMPLE 1

537 g. of allantoin is thoroughly mixed with 463 g. of urocanic acid with vigorous trituration. 2 to 10% water is added and thoroughly mixed forming a semidry mass which is dried for 10 to 12 hours at 160° to 180° F. The complex formed is soluble up to 0.4 to 0.6% in water, and soluble in hot water, and analyzes allantoin 53%±5% and urocanic acid 47%±5%.

EXAMPLE 2

537 g. of allantoin and 463 g. of urocanic acid is dissolved in 3000 cc. of a 10% solution of sodium hydroxide. The solution is acidified with 50% acetic acid to a pH of 4.5 to 5 with constant mixing. The solution is allowed to stand overnight in an ice bath, and allantoin urocanic acid is removed by filtration. The allantoin urocanic acid is washed with distilled water and dried at 160 to 180° F. for 10 to 12 hours forming a complex slightly soluble in water and soluble in hot water. The complex analyzes allantoin 20%±5% and urocanic acid 80%±5%. The example may be repeated using potassium hydroxide or ammonium hydroxide in place of sodium hydroxide.

Infrared spectral analysis establishes that the allantoin urocanic acid complexes of this invention are distinct chemical entities, and this fact is supported by the physical and chemical properties of the complexes. Additionally, aluminum derivatives of the allantoin urocanic acid derivatives may be prepared by reacting allantoin aluminum derivatives with urocanic acid.

The following formulations were made to demonstrate the usefulness of allantoin urocanic acid complexes.

| SUN SCREENING CREAM | |
|---|---|
| INGREDIENTS | WEIGHT PER CENT |
| Ceraphyl 424 | 5.5 |
| Isopropyl Myristate | 13.8 |
| Witconal APM | 3 |
| Promulgen D | 3.5 |
| Cetyl Alcohol | 2.8 |
| Lexemul 561 | 4.1 |
| Myrj 52S | 1.4 |
| Span 65 | 0.4 |
| Tegosept P | 0.1 |
| Escalol 507 | 1.5 |
| Deionized Water | 61 |
| Germall | 0.2 |
| Tegosept M | 0.2 |
| Sodium Benzoate | 0.1 |
| Sorbistat | 0.1 |
| Sequestrene AA | 0.1 |
| Spectra Sorb UV-284 | 1 |
| Urocanic Acid | 0.3 |
| Allantoin Paraminobenzoic Acid | 0.05 |
| Allantoin Urocanate | 0.3 |
| Triethanolamine | 0.6 |
| FD&C Yellow #5 (1%) | 0.1 |
| FD&C Yellow #6 (1%) | 0.04 |
| Perfume RSC #8 | 0.3 |

| SUN SCREEN GEL | |
|---|---|
| Snow White Petrolatum | 5 |
| Allantoin Paramino Benzoic Acid | 0.05 |
| Urocanic Acid | 0.3 |
| Allantoin Urocanate | 0.3 |

| SUN SCREEN GEL | |
|---|---|
| Ozokerite | 7.5 |
| Spermwax | 7.5 |
| Snow White Petrolatum | 36.6 |
| Carnation Oil | 12.8 |
| Butyl Stearate | 19.4 |
| Dipiopylene Glycol Salicylate | 1.5 |
| Giv Tan F | 1.6 |
| Tegosept B | 0.15 |
| Tegosept P | 0.15 |
| Red #17 (K7007) 0.06% in Corn Oil | 4.4 |
| Violet #2 (K7014) 0.06% in Corn Oil | 2.9 |
| Perfume RSC #8 | 0.3 |

| SUNSCREEN CREAM | |
|---|---|
| INGREDIENTS | WEIGHT PER CENT |
| Ceraphyl 424 | 5.5 |
| Isopropyl Myristate | 13.8 |
| Witconal APM | 3 |
| Promulgen D | 3.5 |
| Cetyl Alcohol | 2.8 |
| Lexemul 561 | 4.1 |
| Myrj 52S | 1.4 |
| Span 65 | 0.4 |
| Tegosept P | 0.1 |
| Escalol 507 | 4 |
| Deionized Water | 58.7 |
| Allantoin Paraminobenzoic Acid | 0.05 |
| Germall | 0.2 |
| Tegosept M | 0.2 |
| Sodium Benzoate | 0.1 |
| Sorbistat | 0.1 |
| Sequestrene AA | 0.1 |
| Spectrasorb UV-284 | 1 |
| Allantoin Urocanate | 0.3 |
| Urocanic Acid (Ajimonto) | 0.3 |
| Trimethanolamine | 0.6 |
| Perfume RSC #8 | 0.3 |

What is claimed is:

1. An allantoin urocanic acid complex of the formula $[C_4H_5N_4O_3]_a \cdot [C_6H_6N_2O_2]_b$ wherein a and b are each about 1.

2. An allantoin urocanate complex of the formula $[C_4H_5N_4O_3]_a \cdot [C_6H_6N_2OX]_b$ wherein a and b are each about 1 and refer to the number of mols of each component and X is a member selected from the group consisting of sodium, potassium and ammonium.

* * * * *

UNITED STATES PATENT AND TRADEMARK OFFICE
CERTIFICATE OF CORRECTION

PATENT NO. : 4,181,804
DATED : January 1, 1980
INVENTOR(S) : Sebastian B. Mecca

It is certified that error appears in the above-identified patent and that said Letters Patent are hereby corrected as shown below:

Assignee should be: Carroll Products, Inc., d/b/a Schuylkill Chemical Company, Philadelphia, Pa.

*Signed and Sealed this*

*Eighth* Day of *April 1980*

[SEAL]

*Attest:*

SIDNEY A. DIAMOND

*Attesting Officer*     *Commissioner of Patents and Trademarks*